(12) United States Patent
Dobrovolny

(10) Patent No.: US 6,974,412 B2
(45) Date of Patent: Dec. 13, 2005

(54) CAM-WEDGE LOCKING MECHANISM

(75) Inventor: Walter J. Dobrovolny, St. Paul, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 327 days.

(21) Appl. No.: 10/409,759

(22) Filed: Apr. 9, 2003

(65) Prior Publication Data

US 2003/0191372 A1    Oct. 9, 2003

Related U.S. Application Data

(63) Continuation-in-part of application No. 09/864,681, filed on May 24, 2001, now Pat. No. 6,572,540.

(51) Int. Cl.[7] ............................................... A61B 1/32
(52) U.S. Cl. ...................................... 600/226; 600/215
(58) Field of Search ............................... 600/213, 215, 600/217, 225–230; 74/567, 569, 527; 292/215, 292/222, 224, 185, 187

(56) References Cited

U.S. PATENT DOCUMENTS

| | | | |
|---|---|---|---|
| 3,667,793 A | 6/1972 | Varrin et al. | |
| 3,840,201 A * | 10/1974 | Hasquenoph et al. | .... 244/137.4 |
| 3,965,890 A | 6/1976 | Gauthier | |
| 4,052,980 A | 10/1977 | Grams et al. | |
| 4,064,873 A | 12/1977 | Swenson | |
| 4,407,493 A | 10/1983 | Okolischan | |
| 4,467,896 A | 8/1984 | Sauerwein et al. | |
| 4,667,561 A | 5/1987 | Storey et al. | |
| 4,710,077 A | 12/1987 | Ramunas | |
| 5,472,247 A | 12/1995 | Monson | |
| 5,482,417 A | 1/1996 | Erickson | |
| 5,733,007 A * | 3/1998 | Williams | ..................... 397/367 |
| 5,893,831 A | 4/1999 | Koros et al. | |
| 5,902,233 A | 5/1999 | Farley et al. | |
| 5,976,080 A | 11/1999 | Farascioni | |
| 6,361,488 B1 | 3/2002 | Davison et al. | |
| 2002/0177752 A1 | 11/2002 | Dobrovolny | |

FOREIGN PATENT DOCUMENTS

DE             38 34 358 C1     10/1988

* cited by examiner

Primary Examiner—Eduardo C. Robert
Assistant Examiner—Michael J. Araj
(74) Attorney, Agent, or Firm—Westman, Champlin & Kelly, P.A.

(57) ABSTRACT

The present invention is a mechanism for releasing a positioning device from a locked position. The positioning device has a moveable wedge urged against a rotatable cammed member which permits rotatable travel of the cammed member in only one direction. The releasing mechanism comprises a lever attached to the wedge and engageable with the cammed member. Engaging the lever with the cammed member urges the wedge away from the cammed member to permit rotation of the cammed member in either direction.

19 Claims, 5 Drawing Sheets

CAM-WEDGE LOCKING MECHANISM

CROSS-REFERENCE TO RELATED APPLICATION(S)

This application is a continuation-in-part of U.S. application Ser. No. 09/864,681 filed on May 24, 2001, now U.S. Pat. No. 6,572,540.

BACKGROUND OF THE INVENTION

The present invention relates to a locking mechanism. In particular, the present invention relates to a cam and wedge locking mechanism to selectively position a surgical retractor blade attached to a retractor mounting apparatus.

During many types of surgical procedures it is necessary to use a retractor to hold back tissue proximate a surgical incision. The retractor enables a surgeon to work at and in the surgical incision. Retractors typically include a blade and an arm, such as a shaft, to which the blade is attached. The retractor is generally held in place by attachment to a retractor support apparatus that is positioned over a support surface, such as an operating table. The retractor support apparatus is usually attached to a side rail located along one or more sides of the operating table by a clamping device, such as a fulcrum clamp or a cammed clamp.

Current retractors are not easy to manipulate and position over the surgical incision because the arm is typically a solid inflexible rod. Clamping mechanisms to lock the retractors in a precise location are typically cumbersome and require complex maneuvering that may increase the risk of injury to the patient. Typically, adjustment of the retractor occurs at the clamping device which attaches the retractor to the sides of the operating table. Positioning the retractor at this location remains challenging since the clamping device may be difficult to operate, or be located at a place that may increase the risk of contamination to the patient.

BRIEF SUMMARY OF THE INVENTION

The present invention is an automatic locking mechanism for selectively positioning a retractor blade of a retractor apparatus. The invention includes a retractor blade attached to a cam and wedge locking mechanism. The cam and wedge locking mechanism permits rotational movement of the retractor blade from a first position to a second position, but prohibits reverse rotation while the wedge engages the cam. A releasing mechanism attaches to the locking mechanism to urge the wedge away from the cam, permitting reverse rotation of the retractor blade.

DETAILED DESCRIPTION

Figure 1:
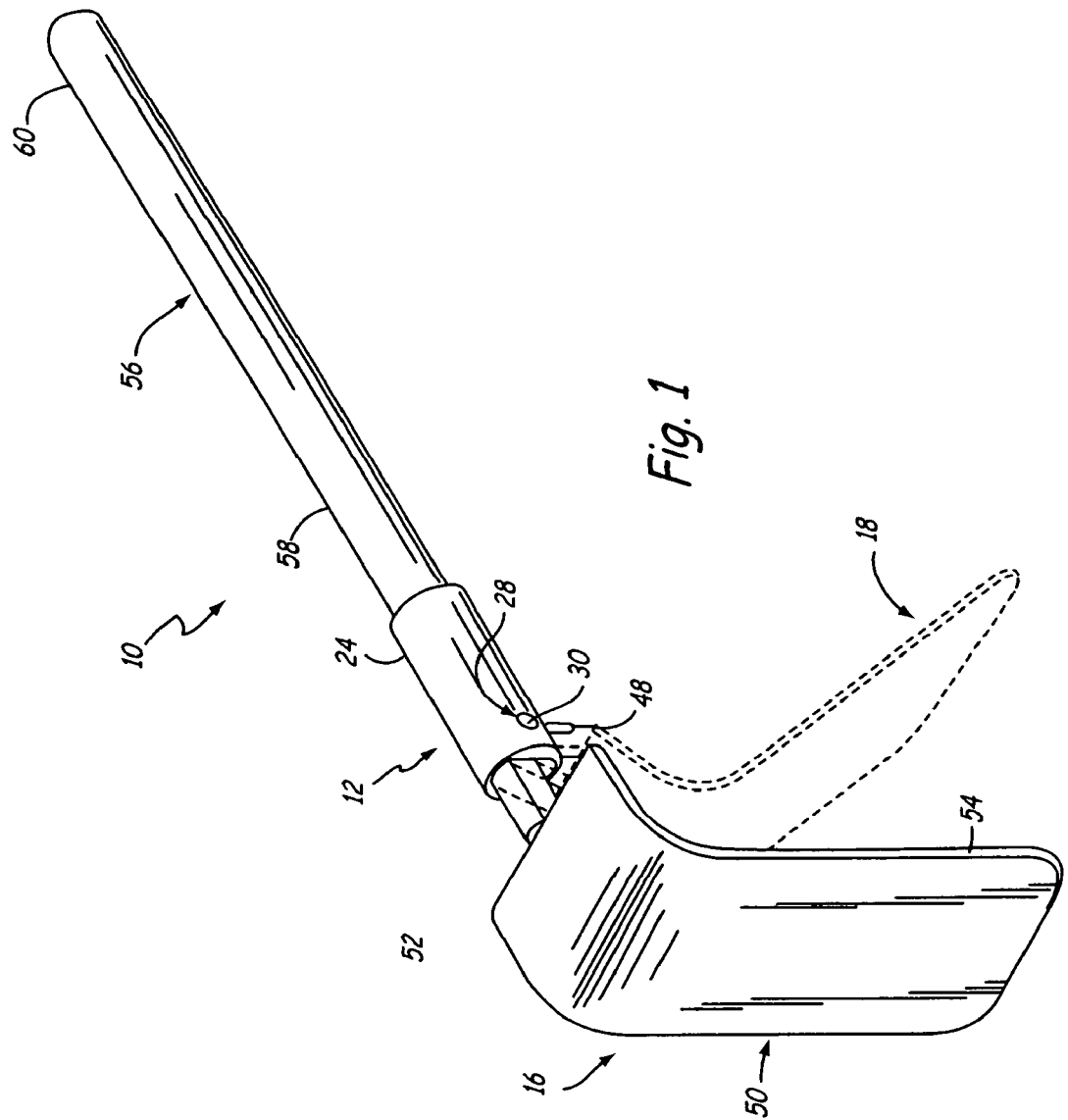
FIG. 1 is a perspective view of a first embodiment of the present invention with a retractor blade in a first position (detailed) and a second position (broken lines).
Figure 2:
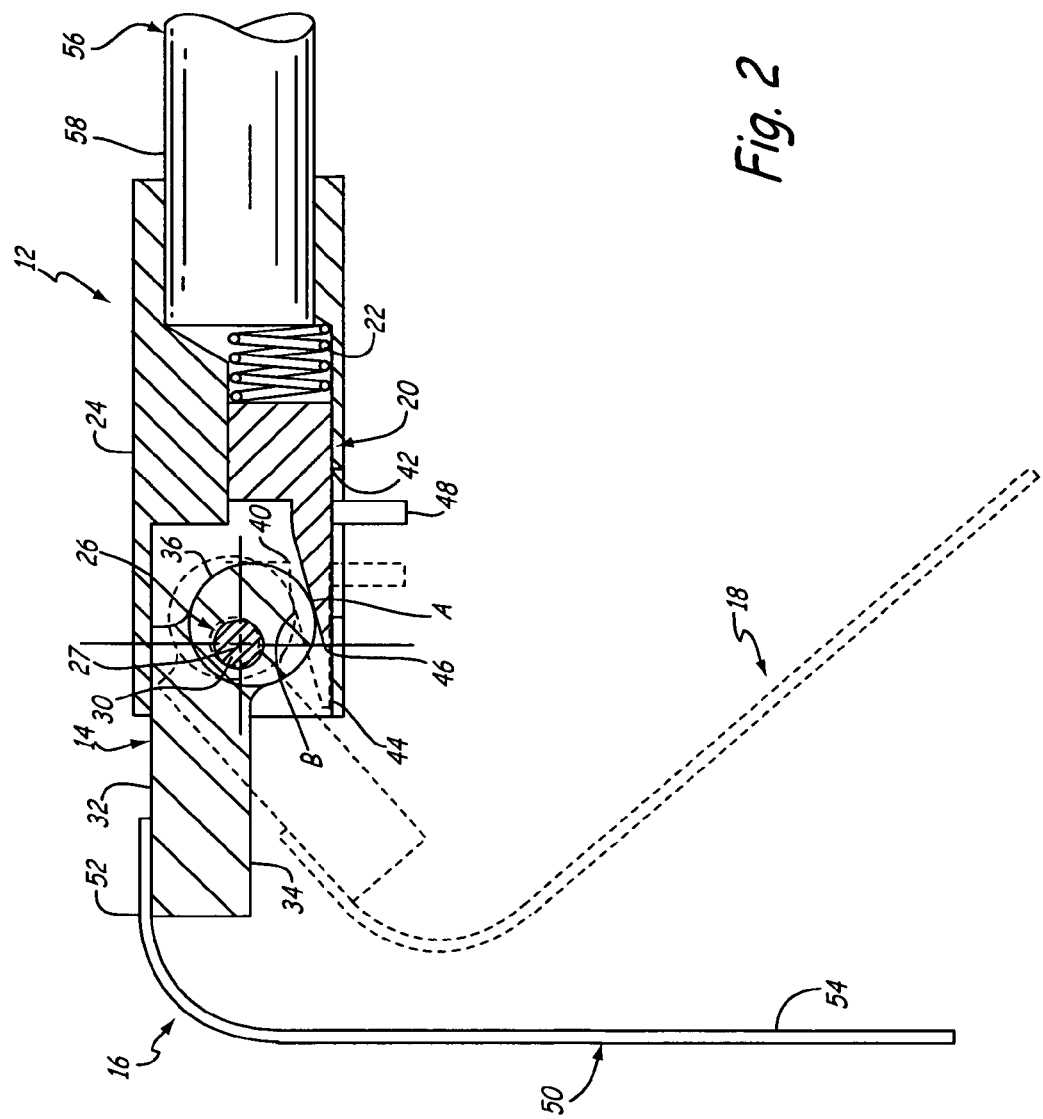
FIG. 2 is a cross-sectional view of the first embodiment of the present invention with the retractor blade in a first position (detailed) and a second position (broken lines).

A retractor apparatus of the present invention is generally indicated at 10 in FIG. 1. A locking mechanism of the present invention is generally indicated at 12. The locking mechanism 12 is designed to automatically permit rotational movement of a retractor blade 50 in one direction only, from a first upright position 16 to a second downward position 18 (shown in broken lines), while the locking mechanism 12 is engaged. The locking mechanism 12 includes a cammed member 14, a wedge member 20, and a spring 22, all enclosed within a housing 24 as illustrated in FIG. 2.

The cammed member 14 includes a through-bore 26, the through-bore 26 defining an axis of rotation 27 for the cammed member 14. The housing 24 includes first and second mating apertures 28, only one of which is illustrated. The mating apertures 28 are aligned with each other by being positioned on opposing wall sections. The cammed member 14 is positioned within the housing 24 such that the through-bore 26 aligns with each mating aperture 28.

A securing pin 30 is inserted through the mating apertures 28 and the through-bore 26 of the cammed member 14, thereby rotatably securing the cammed member 14 to the housing 24. Once secured within the housing 24, the cammed member 14 is freely rotatable between the first upright position 16 and the second downward position 18.

The first upright position 16 is defined by a first top side 32 of the cammed member 14 contacting the housing 24, while the second downward position 18 is defined by a second bottom side 34 of the cammed member 14 contacting the housing 24. It should be noted, however, that the terms 'top' and 'bottom' are arbitrary terms, and are used for illustrative purposes with reference to the Figures.

The cammed member 14 further includes a cammed surface 36 having a decreasing radius from point A to point B as defined from axis 27. The cammed surface 36 may be the result of an eccentric construction (wherein the axis of rotation is in an offset position) or wherein the cam surface 36 is a lobe offset from the axis of rotation or other construction known in the art. Point A is defined as a point on the cammed surface 36 where an inclined surface 40 of the wedge 20 contacts the cammed member 14, corresponding to the cammed member 14 in the first upright position 16. Point B is defined as a point on the cammed surface 36 where the inclined surface 40 of the wedge 20 contacts the cammed member 14, corresponding to the cammed member 14 being in the second downward position 18.

The wedge 20 is a movable member situated within the housing 24 such that the inclined surface 40 of the wedge 20 is capable of contacting the cammed surface 36 of the cammed member 14. The wedge 20 is movable through an infinite number of positions while contacting the wedge 20. A first initial engagement position 42 and a second extended position 44 in broken lines is illustrated in FIG. 2. The first initial engagement position 42 is defined as the position wherein the retractor blade 50 is at a first upright position and the wedge 20 contacts the cammed member 14. The second extended position 44 is defined as the position wherein the retractor blade 50 is at the second downward position 18 and further forward movement of the wedge 20 is prohibited. The wedge is also movable away from the cammed member to a non-engaging position (not shown), wherein the wedge is disengaged from the cammed member 14, and the retractor blade 50 is freely rotatable in either direction.

A height of the inclined surface 40 of the wedge 20 is lowest at a first forward end 46 of the wedge 20, and increases down the length of the wedge 20.

The compressible spring 22 urges the wedge 20 toward the second extended position 44 and against the cammed member 14, thereby contacting the inclined surface 40 of the wedge 20 with the cammed surface 36 of the cammed member 14. A finger tab 48 is attached to the wedge 20. The finger tab 48 allows a user to withdraw the wedge 20 away from contacting the cammed member 14 and toward the first position 42.

In operation, a force is applied to the finger tab 48 which overcomes the force of the compressible spring 22, thereby allowing the wedge 20 to withdraw away from the cammed member 14 toward and even beyond the first initial engaging position 42. Upon moving past the first non-engaging position, the cammed member 14 is freely rotatable in either direction. The retractor blade 50, and thus the cammed member 14 is manually positionable in the first upright position 16 by engaging the finger tab 48 and urging the wedge 20 toward the initial engaging position 42. Upon removal of the force applied to the finger tab 48, the compression spring 22 urges the wedge 20 into contact with the cammed member 14. Upon the wedge 20 engaging the cammed member 14, the cammed member 14 is only rotatable from the first upright position 16 to the second downward position 18, and not in reverse.

As the cammed member 14 rotates from the first position 16 to the second position 18, the decreasing radius from point A to point B of the cammed surface 36 allows the compression spring 22 to urge the wedge 20 toward the second extended position 44, the wedge 20 in continuous contact with the cammed member 14. Reverse-rotation of the cammed member 14 in the direction from the second downward position 18 to the first upward position 16 is not possible because the cammed surface 36 of the cammed member 14 will be forced against the inclined surface 40 of the wedge 20. The relative increase in length of the radius of the cammed member 14, from point B to point A, which defines the cammed surface 36, in conjunction with the increase in height of the wedge 20, prohibits rotatable travel of the cammed member 14 in the reverse direction.

To rotate the cammed member 14 toward the first upright position 16, a force is applied to the finger tab 48 to overcome the force of the compression spring 22 allowing the wedge 20 to slide toward the first initial engaging position 42. When the wedge 20 moves past the initial engaging position 42, the wedge 20 disengages from the cammed member 14, and the cammed member 14 is freely rotatable in either direction. The cammed member 14 can then be positioned in the first upright position 16.

In the preferred embodiment of the present invention, the retractor blade 50 is attached to the cammed member 14. As illustrated in each figure, the retractor blade 50 has a general "L"-shaped configuration with a first leg 52 attached to the cammed member 14. A second leg 54 of the retractor blade extends past the locking mechanism 12, and is configured to retract flesh, such as skin and muscle tissue, in a selected position during a surgical operation. Preferably, the retractor apparatus 10 includes an arm 56 having a proximate end 58 and a distal end 60. The housing 24 of the retractor apparatus 10 is attached to the proximate end 58 of the arm 56.

In use, the retractor blade 50, which is in the first upright position 16, is positioned within the surgical incision, and the distal end 60 of the arm 56 is secured to the operating table (not shown). The surgeon is then able to further position the retractor blade 50 by rotating retractor blade 50, and thus the cammed member 14, toward the second downward position 18.

When a selected position of the retractor blade 50 is obtained, there being an infinite number of selectable positions between the first upright position 16 and the second downward position 18, the retractor blade 50 is held at the selected position due to the automatic locking mechanism 12. A load on the retractor blade 50, which is provided by the retained flesh, tends to urge the retractor blade 50 in the reverse direction toward the first upright position 16. However, when the wedge 20 engages the cammed member 14, rotation in the reverse direction is not permitted, and the flesh is retained at the selected position. Thus, the retractor blade 50 is automatically held at the selected position. The retractor blade 50 can be further positioned to increase access to the operable area if the surgeon desires by further rotating the retractor blade 50, and thus the cammed member 14. Any amount of rotation of the cammed member 14 in the direction of the second downward position 18 will lock the cammed member 14 at that position.

To reposition the retractor blade 50 toward the first upright position 16, a force to overcome the compression spring 22 is applied to the finger tab 48 urging the wedge 20 towards the first initial engaging position 42. As the wedge 20 travels towards the initial engaging position 42, the relative height of the inclined surface 40 decreases allowing the cammed member 14, which has a tendency to rotate toward the first upright position 16 due to the load bearing on the retractor blade 50, to rotate in the reverse direction because of the relatively increasing radius of the cammed surface 36 contacting the relatively decreasing height of the inclined surface 40 of the wedge 20. Any movement of the wedge 20 toward the first non-engaging position will cause the cammed member 14 to reverse rotate and thus affecting the position of the retractor blade 50 towards the first upright position 16.

To remove the retractor apparatus 10 upon completion of the surgical procedure, the finger tab 48 is used to position the wedge 20 past the initial engaging position 42, thus allowing the cammed member 14 to be freely rotatable. The retractor blade 50 is brought to the first upright position 16, and the apparatus 10 is removed from the surgical site.

Figure 3:
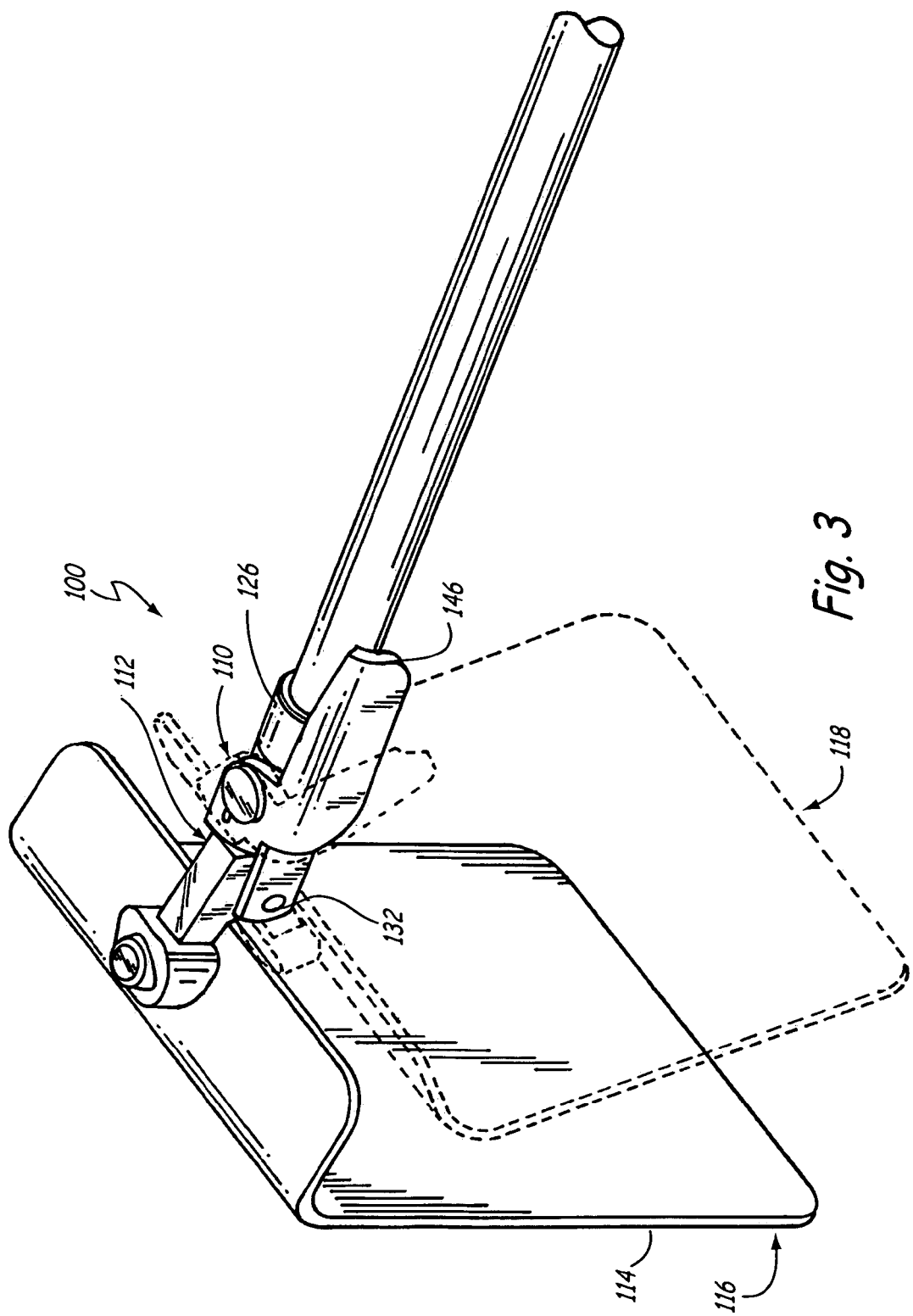
FIG. 3 is a perspective view of a second embodiment of the present invention with a retractor blade in a first position (detailed) and a second position (broken lines) along with a lever of a releasing mechanism in a non-engaging position (broken lines) and an engaging position (detailed).
Figure 4:
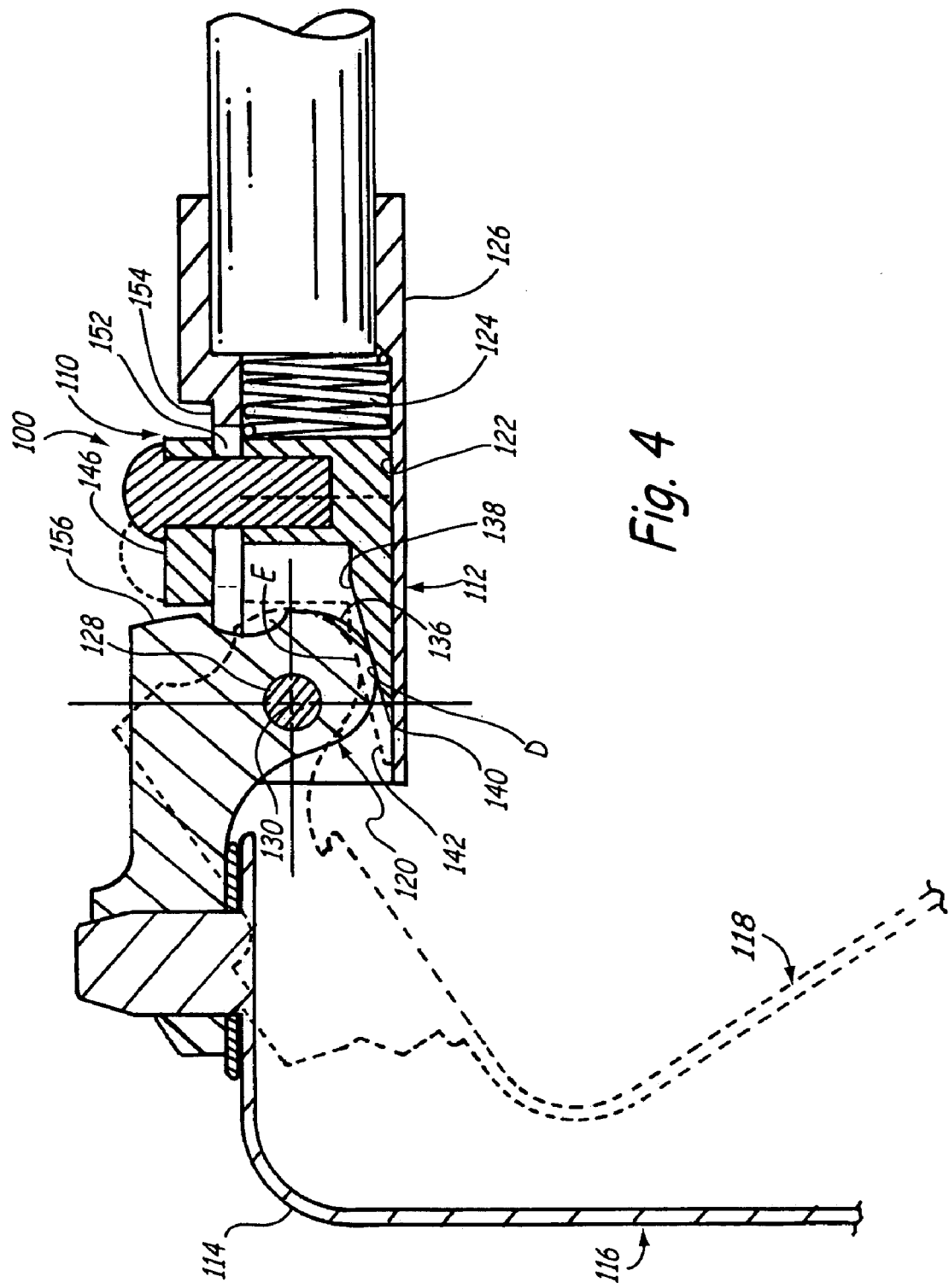
FIG. 4 is a cross-sectional view of the second embodiment of the present invention with the retractor blade in a first position (detailed) and a second position (broken lines).
Figure 5:
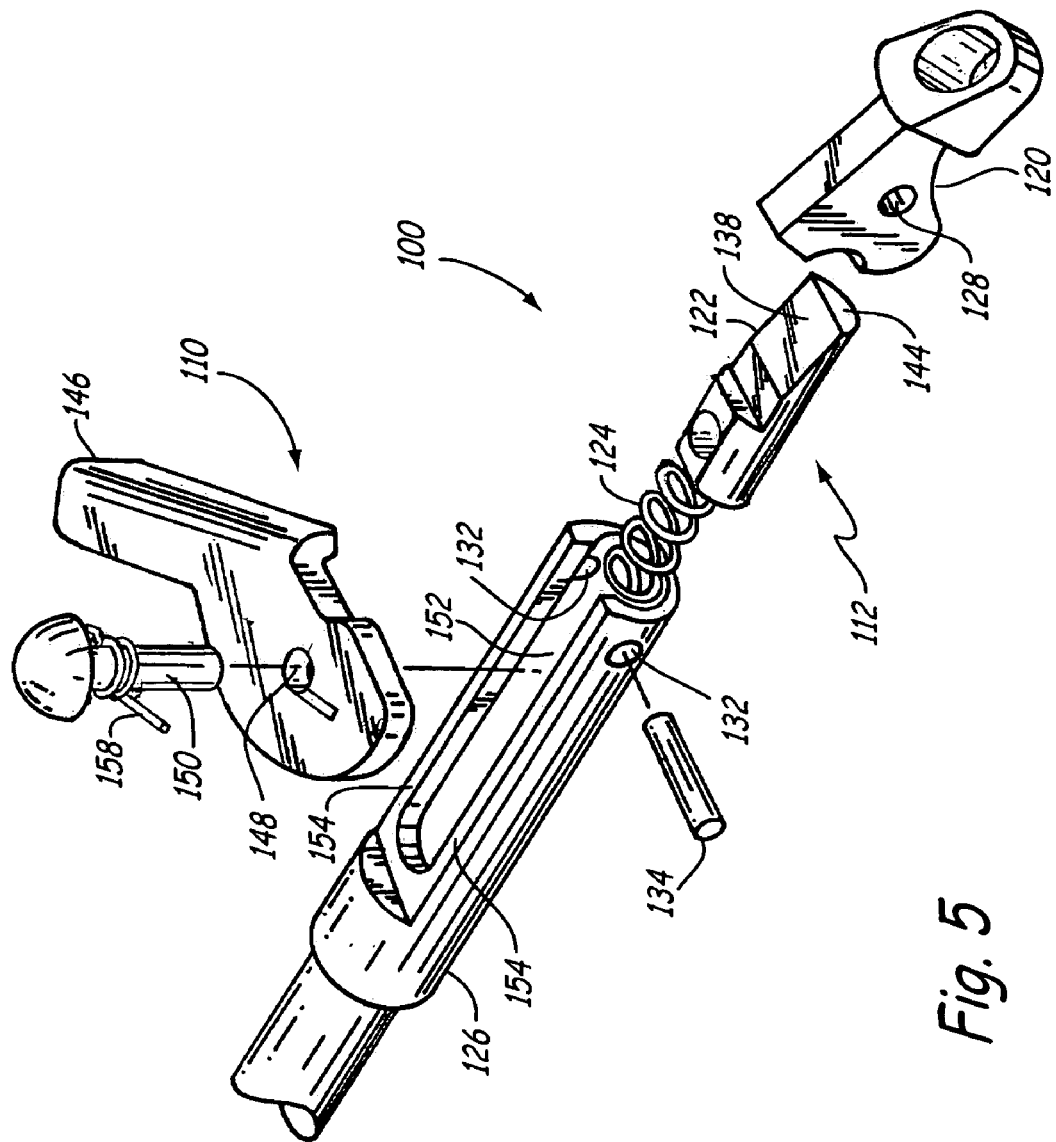
FIG. 5 is a exploded perspective view of the second embodiment of the present invention.

An alternative embodiment of the present invention is generally indicated at 100 in FIGS. 3 through 5. A releasing mechanism for use with the alternative embodiment 100 is generally indicated at 110 while a locking mechanism is generally indicated at 112. The locking mechanism 112 is designed to automatically permit rotational movement of a retractor blade 114 in one direction only, from a first upright position 116 to a second downward position 118 (shown in broken lines), while the locking mechanism 112 is engaged. The releasing mechanism 110 provides a means to selectively position the retractor blade between the second downward position 118 to the first upright position 116 when a retraction force is exerted on the retractor blade 114.

The locking mechanism 112 includes a cammed member 120, a wedge 122, and a spring 124, all enclosed within a housing 126. The cammed member 120 includes a throughbore 128 an axis of rotation 130 for the cammed member 120. The housing 126 includes first and second mating apertures 132, only one of which is illustrated. The mating apertures 132 are aligned with each other by being positioned on opposing wall sections of the housing 126. The cammed member 120 is positioned within the housing 126 such that the through-bore 128 aligns with each mating aperture 132.

A securing pin 134 inserts through the mating apertures 132 and the through-bore 128 of the cammed member 120, thereby rotatably securing the cammed member 120 to the housing 126. Once secured within the housing 126, the cammed member 120 is freely rotatable between the first upright position 116 and the second downward position 118.

The cammed member 120 further includes a cammed surface 136 having a decreasing radius from point D to point E as defined from axis 130. The cammed surface 136 may be the result of an eccentric construction (wherein the axis of rotation is in an offset position) or wherein the cam surface 136 is a lobe offset from the axis of rotation or other construction known in the art. Point D is defined as a point on the cammed surface 136 where an inclined surface 138 of the wedge 122 contacts the cammed member 120, corresponding to the cammed member 120 in the first upright position 116. Point E is defined as a point on the cammed surface 136 where the inclined surface 138 of the wedge 122 contacts the cammed member 120, corresponding to the cammed member 120 being in the second downward position 118.

The wedge 122 is a movable member situated within the housing 126 such that the inclined surface 138 of the wedge 122 is capable of contacting the cammed surface 136 of the cammed member 120. The wedge 122 is movable through an infinite number of positions while contacting the cammed member 120. The infinite number of positions is best explained by a first initial engagement position 140 and a second extended position 142. As illustrated in FIG. 4, the first initial engagement position 140 is defined as the position wherein the retractor blade 114 is at the first upright position 116 and the wedge 122 contacts the cammed member 120. The second extended position 142 is defined as the position wherein the retractor blade 114 is at the second downward position 118 and further forward movement of the wedge 122 is prohibited. The wedge 122 is also movable away from the cammed member 120 to a non-engaging position (not shown), wherein the wedge 122 is disengaged from the cammed member 120, and the retractor blade 114 is freely rotatable in either direction. A height of the inclined surface 138 of the wedge 122 is lowest at a first forward end 144 of the wedge 122, and increases down the length of the wedge 122.

The compressible spring 124 urges the wedge 122 toward the second extended position 142 and against the cammed member 120, thereby contacting the inclined surface 138 of the wedge 122 with the cammed surface 136. The releasing mechanism 110 pivotally attaches to the wedge 122. The releasing mechanism 110 allows a user to incrementally urge the wedge 122 toward the first position 140, away from contacting the cammed member 120, thus incrementally allowing the retractor blade 114 to travel from the second position 118 toward the first position 116.

The releasing mechanism 110 includes a lever 146 having an aperture 148 through which a pin 150 extends to pivotally secure the lever 146 to the wedge 122. The pin 150 slidably disposes within a slotted aperture 152 positioned within the housing 126. The slotted aperture 152 includes flattened surfaces 154 on either side upon which the lever 146 slidably engages. As illustrated in FIG. 3, the lever 146 is pivotable between a non-engaging position (dashed) and an engaging position (solid). Positioning the lever 146 from the non-engaging position toward the engaging position, the lever 146 engages an abutting surface 156 of the cammed member 120. A torsional spring 158 is provided to retain the lever 146 in the non-engaging position during use to prevent the lever 146 from unwanted engagement with the abutting surface 156.

In operation, the releasing mechanism 110 disengages the wedge 122 from the cammed member 120. The lever 146 is positioned to fully engage the abutting surface 156, which overcomes the force of the compressible spring 124, thereby allowing the wedge 122 to withdraw away from the cammed member 120 toward and even beyond the first initial engaging position 140. Upon moving past the first non-engaging position, the cammed member 120 is rotatable in either direction against the frictional force of the lever 146 engaging the abutting surface 156. The retractor blade 114, and thus the cammed member 120, is manually positionable to the first upright position 116. Upon releasing the lever 146, the torsional spring 158 urges the lever 146 into the non-engaging position, and the compression spring 124 urges the wedge 122 into contact with the cammed member 120. Upon the wedge 122 engaging the cammed member 120, the cammed member 120 is only rotatable from the first upright position 116 to the second downward position 118, and not in reverse.

As the cammed member 120 rotates from the first position 116 to the second position 118, the decreasing radius from point D to point E of the cammed surface 136 allows the compression spring 124 to urge the wedge 122 toward the second extended position 142, the wedge 122 being in continuous contact with the cammed surface 136. Reverse-rotation of the cammed member 120 in the direction from the second downward position 118 to the first upward position 116 is not possible because the cammed surface 136 of the cammed member 120 will be forced against the inclined surface 138 of the wedge 122. The relative increase in length of the radius of the cammed member 120, from point E to point D, which defines the cammed surface 136, in conjunction with the increase in height of the wedge 122, prohibits rotatable travel of the cammed member 120 in the reverse direction.

To position the retractor blade 114 toward the first upright position 116, the releasing mechanism 110 is enacted to urge the wedge 122 to slide toward the first initial engaging position 140. The lever 146 is positioned to engage the abutting surface 156 of the cammed member 120. Upon overcoming the force of the compression spring 124, the wedge 122 will travel away from the cammed member 120, allowing the cammed member 120 to slightly rotate and reposition the retractor blade 114 in an infinite number of positions. As the wedge 122 travels toward the initial engaging position 140, the lever 146 slides upon the flattened surfaces 154 of the housing such that the contact with the lever 146 and the abutting surface 156 coincide with the contact of the traveling inclined surface 138 and cammed surface 136. When the wedge 122 reaches the initial engaging position 140, the lever 146 must manually disengage the wedge 122 from the cammed member 120 in order for the cammed member 120 to be rotatable in either direction to position the retractor blade 114.

The retractor blade 114, and use of the retractor apparatus 100 in a surgical setting, is the same as described in relation to the embodiment of retractor apparatus 10.

Although the present invention has been described with reference to preferred embodiments, workers skilled in the art will recognize that changes may be made in form and detail without departing from the spirit and scope of the invention.

What is claimed is:

1. A positioning device comprising:
    a cam rotatable in a first direction and a second direction;
    a wedge engageable with the cam to be rotatable in the first direction only; and
    a lever attached to the wedge, the lever engageable with the cam to urge the wedge away from the cam, thereby permitting rotatable travel of the cam in the second direction.

2. The positioning device of claim 1 wherein the cam comprises:
    a cam surface engageable with the wedge; and
    an abutting surface engageable with the lever.

3. The positioning device of claim 1 wherein the lever pivotally attaches to the wedge.

4. The positioning device of claim 1 and further comprising a spring to urge the wedge against the cam.

5. The positioning device of claim 1 wherein the lever is pivotable between a non-engaging positioning and an engaging position.

6. The positioning device of claim 5 and further comprising a torsional spring to urge to the lever toward the non-engaging position.

7. The positioning device of claim 1 wherein the lever is positionable between a first position wherein the lever is disengaged from the cam and a second position wherein the lever engages the cam and further comprising a spring to urge the lever toward the first position.

8. In combination a positioning device and mechanism for releasing the positioning device from a locked position, the positioning device having a moveable wedge urged against a rotatable cammed member permitting rotatable travel of the cammed member in only one direction while in the locked position, the mechanism comprising a lever attached to the wedge and engageable with the cammed member, wherein engaging the lever with the cammed member urges the wedge away from the cammed member to permit rotation of the cammed member in either direction.

9. The combination of claim 8 wherein the lever pivotally attaches to the wedge.

10. The combination of claim 8 and further comprising a torsional spring to urge the lever away from the cammed member.

11. The combination of claim 8 wherein the cammed member comprises:
    a cam surface engageable with the wedge; and
    an abutting surface engageable with the lever.

12. The combination of claim 8 and further comprising a spring to urge the wedge against the cam.

13. The combination of claim 8 wherein the lever is pivotable between a non-engaging positioning and an engaging position.

14. The combination of claim 13 and further comprising a torsional spring to urge to the lever toward the non-engaging position.

15. A positioning mechanism for securing a retractor in a selected position, the positioning mechanism comprising:
    a pivotable member having a cammed surface;
    a moveable wedge having an inclined surface engageable against he cammed surface, and
    a lever attached to the wedge and engageable against the pivotable member, whereupon urging the inclined surface of the wedge against the cammed surface of the pivotable member retains the retractor in the selected position, wherein engaging the lever against the pivotable member urges the wedge away from the pivotable member to permit rotation of the pivotable member.

16. The positioning mechanism of claim 15 and further comprising a compression spring for urging the wedge against the pivotable member.

17. The positioning mechanism of claim 15 and further comprising a torsional spring for urging the lever away from the pivotable member.

18. The positioning mechanism of claim 15 and further comprising a housing, wherein the wedge disposes within the housing and wherein the lever slidably dispose upon the housing.

19. The positioning mechanism of claim 15 wherein the lever pivotally attaches to the wedge.

* * * * *